(12) United States Patent
Kato

(10) Patent No.: US 8,987,675 B2
(45) Date of Patent: Mar. 24, 2015

(54) RADIATION DETECTING APPARATUS AND RADIATION IMAGING APPARATUS

(71) Applicant: GE Medical Systems Global Technology Company, LLC, Waukesha, WI (US)

(72) Inventor: Mai Kato, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 14/011,477

(22) Filed: Aug. 27, 2013

(65) Prior Publication Data

US 2014/0064443 A1 Mar. 6, 2014

(30) Foreign Application Priority Data

Aug. 28, 2012 (JP) .................. 2012-187687

(51) Int. Cl.
*G01T 1/02* (2006.01)
*G21K 1/02* (2006.01)
*A61B 6/00* (2006.01)

(52) U.S. Cl.
CPC .............. *G21K 1/025* (2013.01); *A61B 6/4429* (2013.01)
USPC ..................................................... 250/363.1

(58) Field of Classification Search
CPC ................................................. G01T 1/1648
USPC ..................................................... 250/363.1
See application file for complete search history.

(56) References Cited

U.S. PATENT DOCUMENTS

| 4,203,037 | A | 5/1980 | Gur et al. |
| 4,663,531 | A | 5/1987 | Ruike |
| 6,052,436 | A | 4/2000 | Huttner et al. |
| 7,526,875 | B2 | 5/2009 | Freund |
| 8,483,362 | B2 | 7/2013 | Freund |
| 2004/0011960 | A1 | 1/2004 | Morooka et al. |
| 2012/0307963 | A1* | 12/2012 | Watanabe et al. ................. 378/7 |

FOREIGN PATENT DOCUMENTS

| JP | 2002328175 | 11/2002 |
| JP | 2005509891 A | 4/2005 |
| JP | 2012137443 | 7/2012 |

* cited by examiner

*Primary Examiner* — David Porta
*Assistant Examiner* — Hugh H Maupin
(74) *Attorney, Agent, or Firm* — Armstrong Teasdale LLP

(57) ABSTRACT

A radiation detecting apparatus is provided. The radiation detecting apparatus includes a pair of rails extending in a channel direction, a plurality of collimator modules provided in the pair of rails and arranged in the channel direction, each collimator module having a plurality of collimator plates arranged in the channel direction, and a plurality of detector modules provided on a radiation outgoing side of the collimator modules and arranged in the channel direction, wherein each of the collimator modules has a pair of alignment pins extending along an irradiation direction, wherein the rails include a surface of placement for each collimator module, the surface of placement formed with one of concave holes and grooves in which first ends of the alignment pins are fitted, and wherein each of the detector modules has one of concave holes and through holes in which second ends of the alignment pins are fitted.

20 Claims, 7 Drawing Sheets

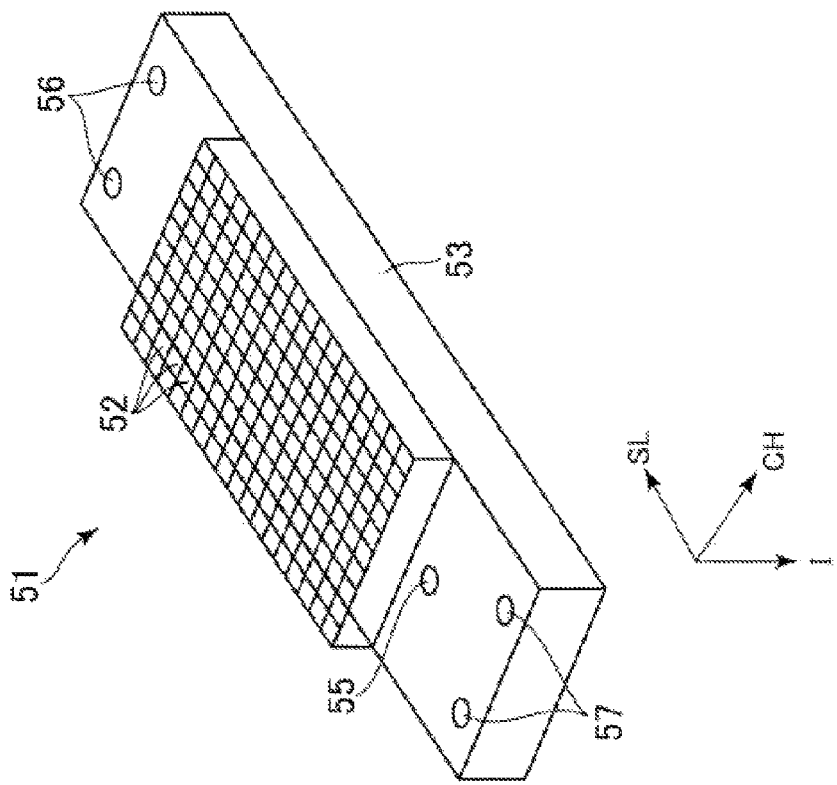
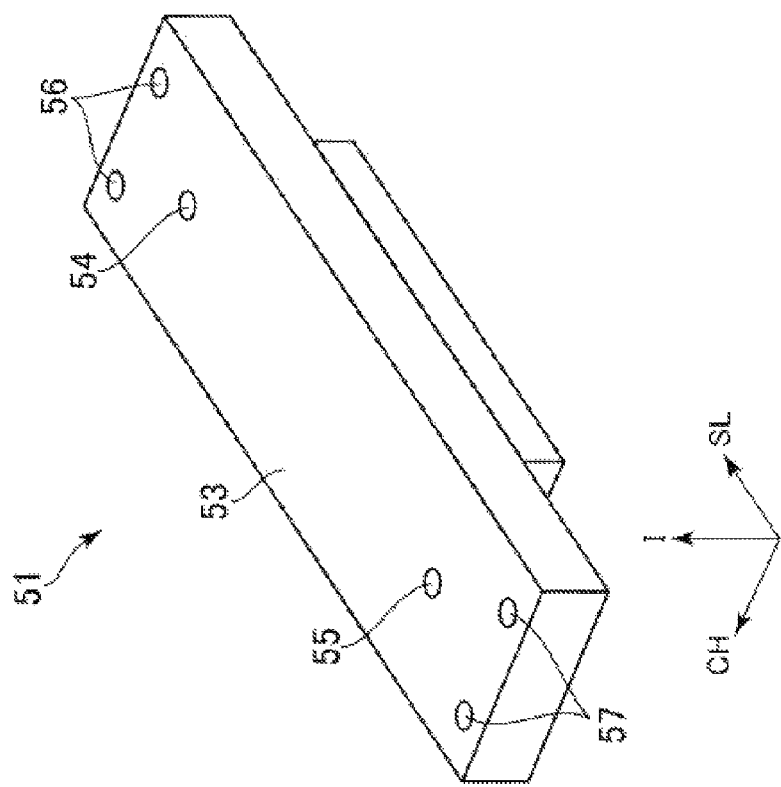
FIG. 4A
FIG. 4B

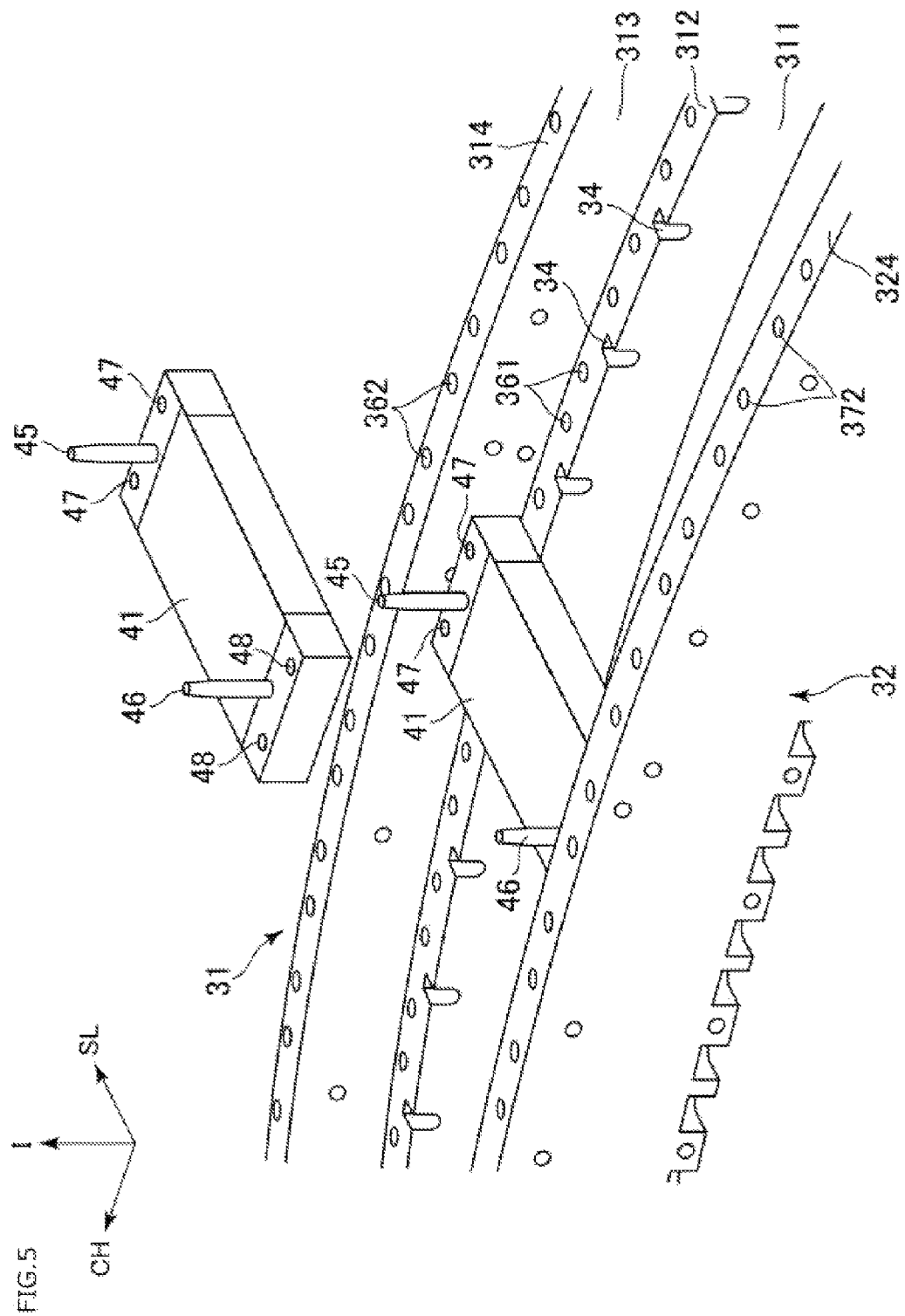

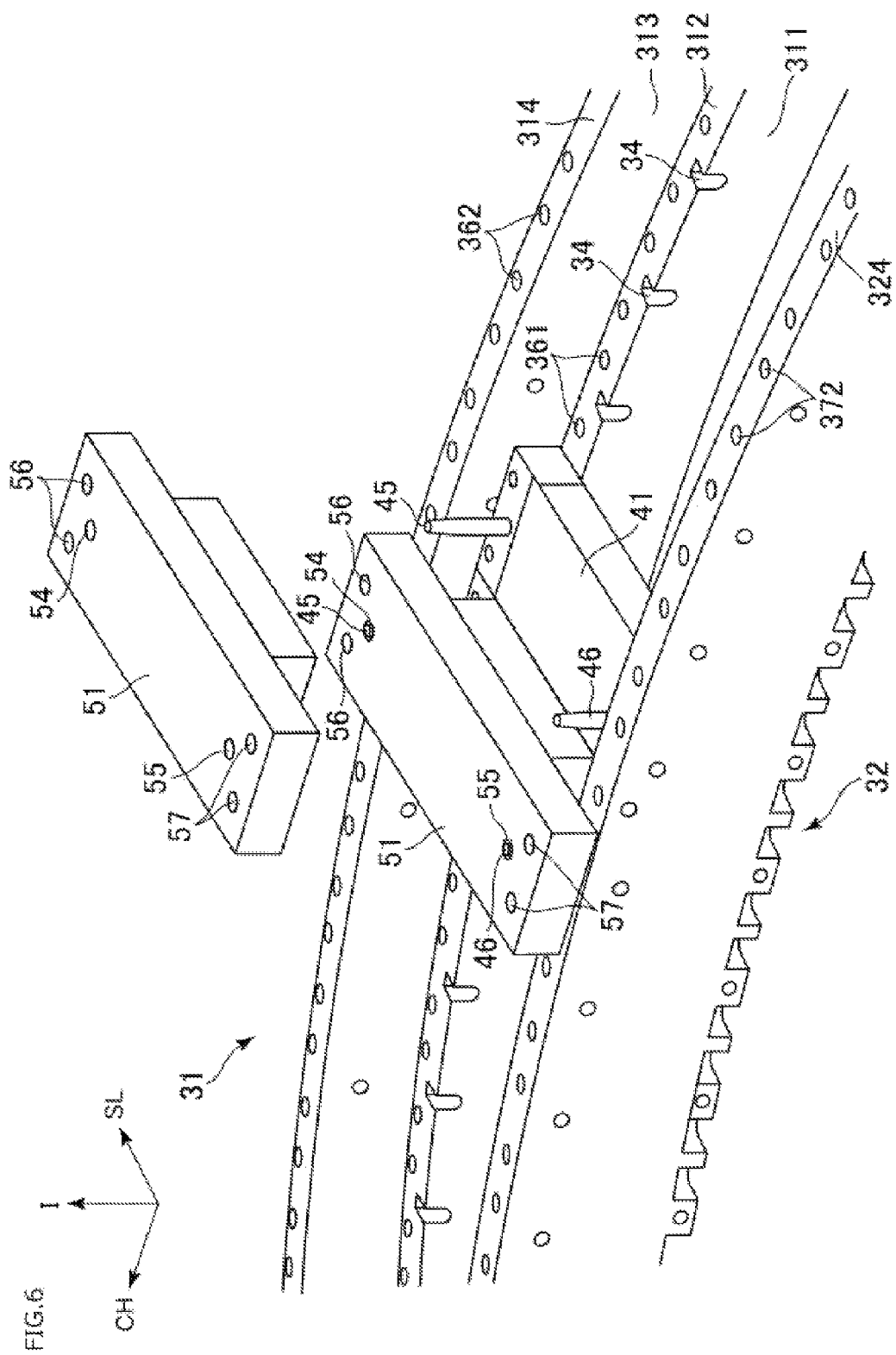

RADIATION DETECTING APPARATUS AND RADIATION IMAGING APPARATUS

CROSS REFERENCE TO RELATED APPLICATIONS

This application claims the benefit of Japanese Patent Application No. 2012-187687 filed Aug. 28, 2012, which is hereby incorporated by reference in its entirety.

BACKGROUND OF THE INVENTION

The present invention relates to a radiation detecting apparatus and a radiation imaging apparatus, and particularly to a technology of alignment between a collimator and a detector.

An X-ray CT (Computed Tomography) apparatus is equipped with an X-ray source and an X-ray detecting apparatus. The X-ray detecting apparatus is equipped with a detector comprised of a plurality of detecting elements, and a collimator for the elimination of scattered radiation, which is comprised of a plurality of collimator plates.

In order to improve the X-ray incoming efficiency and detection characteristics of each detecting element, there is a need to highly accurately align the detecting elements and the collimator plates with each other.

On the other hand, there has heretofore been adopted a method of inserting collimator plates into slits of comb-like collimator plate holding parts attached to rails to perform their positioning and positioning detector modules in other slots formed in the rails through pins (refer to, for example, Japanese Unexamined Patent Publication No. 2002-328175, FIG. 3, FIG. 4, FIG. 7, etc.).

In the above method, a reference for positioning each collimator plate and a reference for positioning each detecting element have been provided separately. Therefore, tolerances accumulate from their positioning, and a position displacement between the detecting element and the collimator plate may occur, thus resulting in a limit to an increase in the accuracy of their alignment.

With the foregoing in view, there has been a demand for a technology capable of more accurately aligning the detecting elements and the collimator plates with one another.

BRIEF DESCRIPTION OF THE INVENTION

In a first aspect, a radiation detecting apparatus is provided. The radiation detecting apparatus includes a pair of rails that extends in a channel direction, a plurality of collimator modules which are provided in the pair of rails in the channel direction and each of which has a plurality of collimator plates arranged in the channel direction, and a plurality of detector modules which are provided on the radiation outgoing side of the collimator modules in the channel direction and each of which has a plurality of detecting elements arranged in the channel direction, in which each of the collimator modules has a pair of alignment pins extending along an irradiation direction of radiation, in which said rails are formed with concave holes or grooves at each surface of placement for said each collimator module in which one ends of the alignment pins are fitted, and in which each of the detector modules has concave holes or through holes in which the other ends of the alignment pins are fitted.

In a second aspect, the radiation detecting apparatus according to the first aspect is provided, in which the concave holes or grooves in which the one ends of the alignment pins are fitted, are formed by being dug in members which form the rails.

In a third aspect, the radiation detecting apparatus according to the first or second aspect is provided, in which each of the collimator modules is fastened to the rails with screws in a state in which the one ends of the alignment pins have been fitted in the concave holes or grooves of the rails.

In a fourth aspect, the radiation detecting apparatus according to any one of the first through third aspects is provided, in which each of the detector modules is fastened to the rails with screws in a state in which the other ends of the alignment pins have been fitted in the concave holes or through holes of each of the detector modules.

In a fifth aspect, the radiation detecting apparatus according to any one of the first through fourth aspects is provided, in which the alignment pins are provided in positions located in the neighborhood of a center in the channel direction, of each of the collimator modules and shifted in the channel direction from the center.

In a sixth aspect, the radiation detecting apparatus according to any one of the first through fifth aspects is provided, in which each of the collimator modules has a pair of blocks which support the collimator plates with the collimator plates interposed therebetween in a slice direction, and in which the alignment pins are provided in the pair of blocks.

In a seventh aspect, the radiation detecting apparatus according to the sixth aspect is provided, in which the alignment pins are press-fitted into and fixed to through holes formed in the pair of blocks.

In an eighth aspect, the radiation detecting apparatus according to any one of the first through seventh aspects is provided, in which the rails have planes opposite to each other in the slice direction, and in which the concave grooves are formed by being dug in the placement surfaces and the planes.

In a ninth aspect, the radiation detecting apparatus according to any one of the first through seventh aspects is provided, in which each of the detector modules has a support body which supports the detecting elements and a signal processing unit for processing signals outputted from the detecting elements, and in which the concave holes or through holes of each of the detector modules are formed in the support body.

In a tenth aspect, a radiation imaging apparatus including a radiation detecting apparatus is provided. The radiation detecting apparatus includes a pair of rails that extends in a channel direction, a plurality of collimator modules which are provided in the pair of rails in the channel direction and each of which has a plurality of collimator plates arranged in the channel direction, and a plurality of detector modules which are provided on the radiation outgoing side of the collimator modules in the channel direction and each of which has a plurality of detecting elements arranged in the channel direction, in which each of the collimator modules has a pair of alignment pins extending along an irradiation direction of radiation, in which said rails are formed with concave holes or grooves at each surface of placement for said each collimator module in which one ends of the alignment pins are fitted, and in which each of the detector modules has concave holes or through holes in which the other ends of the alignment pins are fitted.

In an eleventh aspect, the radiation imaging apparatus described in the tenth aspect is provided, in which the concave holes or grooves in which the one ends of the alignment pins are fitted, are formed by being dug in members which form the rails.

In a twelfth aspect, the radiation imaging apparatus according to the eleventh aspect is provided, in which each of the collimator modules is fastened to the rails with screws in a state in which the one ends of the alignment pins have been fitted in the concave holes or grooves of the rails.

In a thirteenth aspect, the radiation imaging apparatus according to the ninth or twelfth aspect is provided, in which each of the detector modules is fastened to the rails with screws in a state in which the other ends of the alignment pins have been fitted in the concave holes or through holes of each of the detector modules.

In a fourteenth aspect, the radiation imaging apparatus according to any one of the tenth through thirteenth aspects is provided, in which the alignment pins are provided in positions located in the neighborhood of a center in the channel direction, of each of the collimator modules and shifted in the channel direction from the center.

In a fifteenth aspect, the radiation imaging apparatus according to any one of the tenth through fourteenth aspects is provided, in which each of the collimator modules has a pair of blocks which support the collimator plates with the collimator plates interposed therebetween in a slice direction, and in which the alignment pins are provided in the pair of blocks.

In a sixteenth aspect, the radiation imaging apparatus according to the fifteenth aspect is provided, in which the alignment pins are press-fitted into and fixed to through holes formed in the pair of blocks.

In a seventeenth aspect, the radiation imaging apparatus according to any one of the tenth through sixteenth aspects is provided, in which the rails have planes opposite to each other in the slice direction, and in which the concave grooves are formed by being dug in the placement surfaces and the planes.

In an eighteenth aspect, the radiation imaging apparatus according to any one of the tenth through seventeenth aspects is provided, in which each of the detector modules has a support body which supports the detecting elements and a signal processing unit for processing signals outputted from the detecting elements, and in which the concave holes or through holes of each of the detector modules are formed in the support body.

In a nineteenth aspect, the radiation imaging apparatus according to any one of the tenth through eighteenth aspects is provided, which performs radiation tomographic imaging.

According to the above aspects, since collimator modules and detector modules that correspond to one another are positioned on the basis of the same alignment pins, tolerances at their positioning can be prevented from being accumulated, and detecting elements and collimator plates can more accurately be aligned with one another.

BRIEF DESCRIPTION OF THE DRAWINGS

FIGS. 4A and 4B are diagrams illustrating a configuration of a detector module.

FIG. 5 is a diagram showing the manner in which the collimator module is positioned using alignment pins.

FIG. 6 is a diagram showing the manner in which the detector module is positioned using alignment pins.

DETAILED DESCRIPTION OF THE INVENTION

An exemplary embodiment will hereinafter be described.

Figure 1:
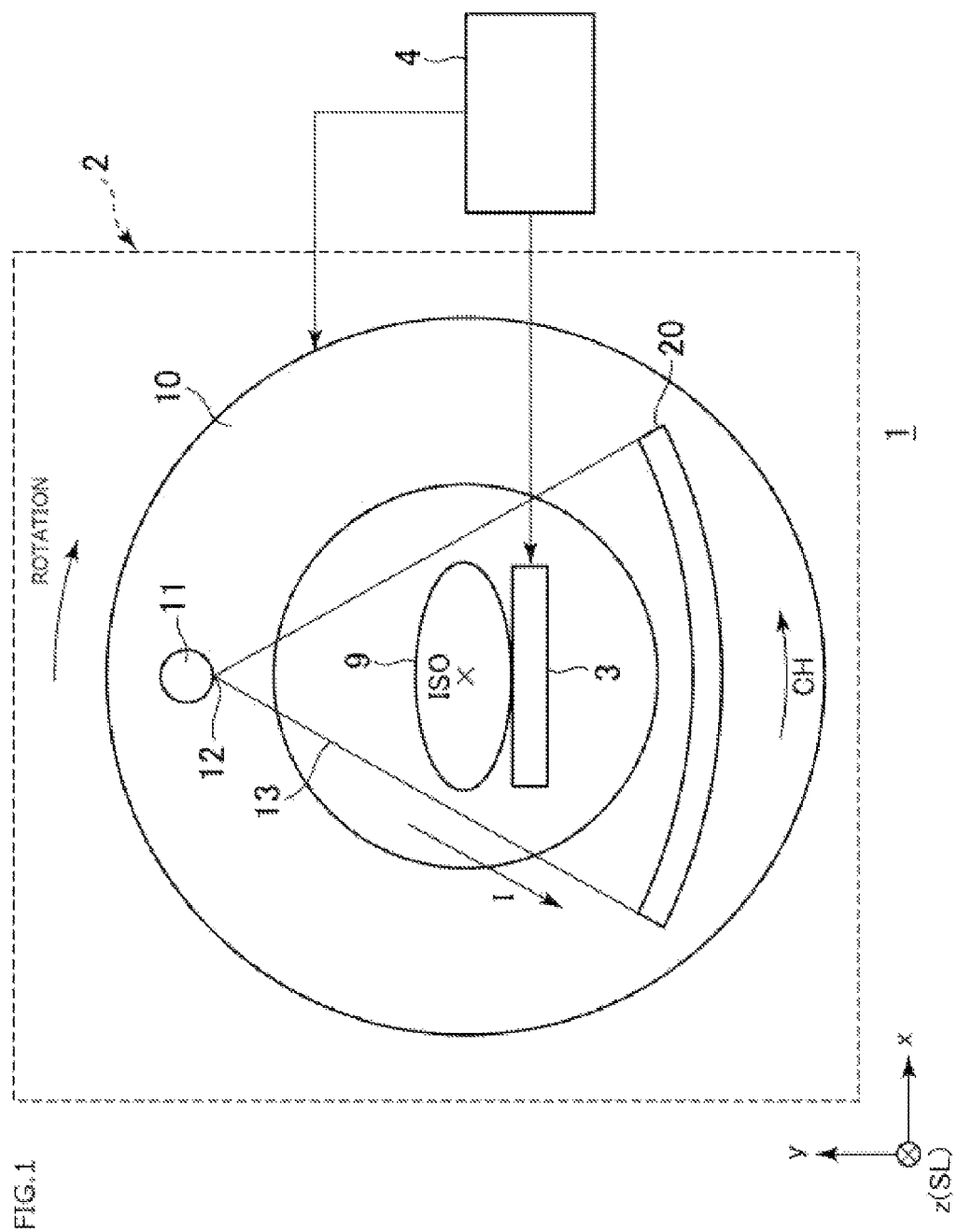
FIG. 1 is a diagram schematically showing a configuration of an X-ray CT apparatus according to an exemplary embodiment.

FIG. 1 is a diagram schematically showing a configuration of an X-ray CT apparatus according to the exemplary embodiment. As shown in FIG. 1, the X-ray CT apparatus 1 has a scan gantry 2 which scans a subject 9 being targeted for imaging to acquire projection data, and an imaging table 3 which carries the subject 9 in a bore of the scan gantry 2. Further, the X-ray CT apparatus 1 has an operation console 4 which controls the respective parts that configure the X-ray CT apparatus 1 to scan and reconstructs an image, based on the projection data acquired by the scan.

The imaging table 3 has a cradle which places the subject thereon and causes the cradle to be elevated and linearly moved horizontally.

The operation console 4 has an input device which accepts an input from an operator, and a monitor which displays each image thereon. Also, the operation console 4 has thereinside a central processing unit which performs control of respective parts for acquiring projection data of the subject, a three-dimensional image reconstructing process, etc., a data acquisition buffer which acquires or collects data acquired by the scan gantry 2, and a storage device which stores programs, data, etc. therein.

The scan gantry 2 has an annular rotating section 10 which rotates about the subject 9. The rotating section 10 is equipped with an X-ray tube 11 and an X-ray detecting apparatus 20 disposed opposite to each other with the bore interposed therebetween. The X-ray detecting apparatus 20 has a curved shape that extends in a channel direction (CH direction) in the drawing. The scan is performed by applying X-rays 13 in their radiation direction (I direction) from an X-ray focal point 12 of the X-ray tube 11 while rotating the rotating section 10 and detecting the X-rays transmitted through the subject 9 by the X-ray detecting apparatus 20. Incidentally, the direction (fan angle direction) of expansion of fan-shaped X-rays parallel to the rotational surface of the rotating section 10 and applied is assumed to be the channel direction (CH direction), and the direction of a rotational axis of the rotating section 10 is assumed to be a slice direction (SL direction).

Figure 2:
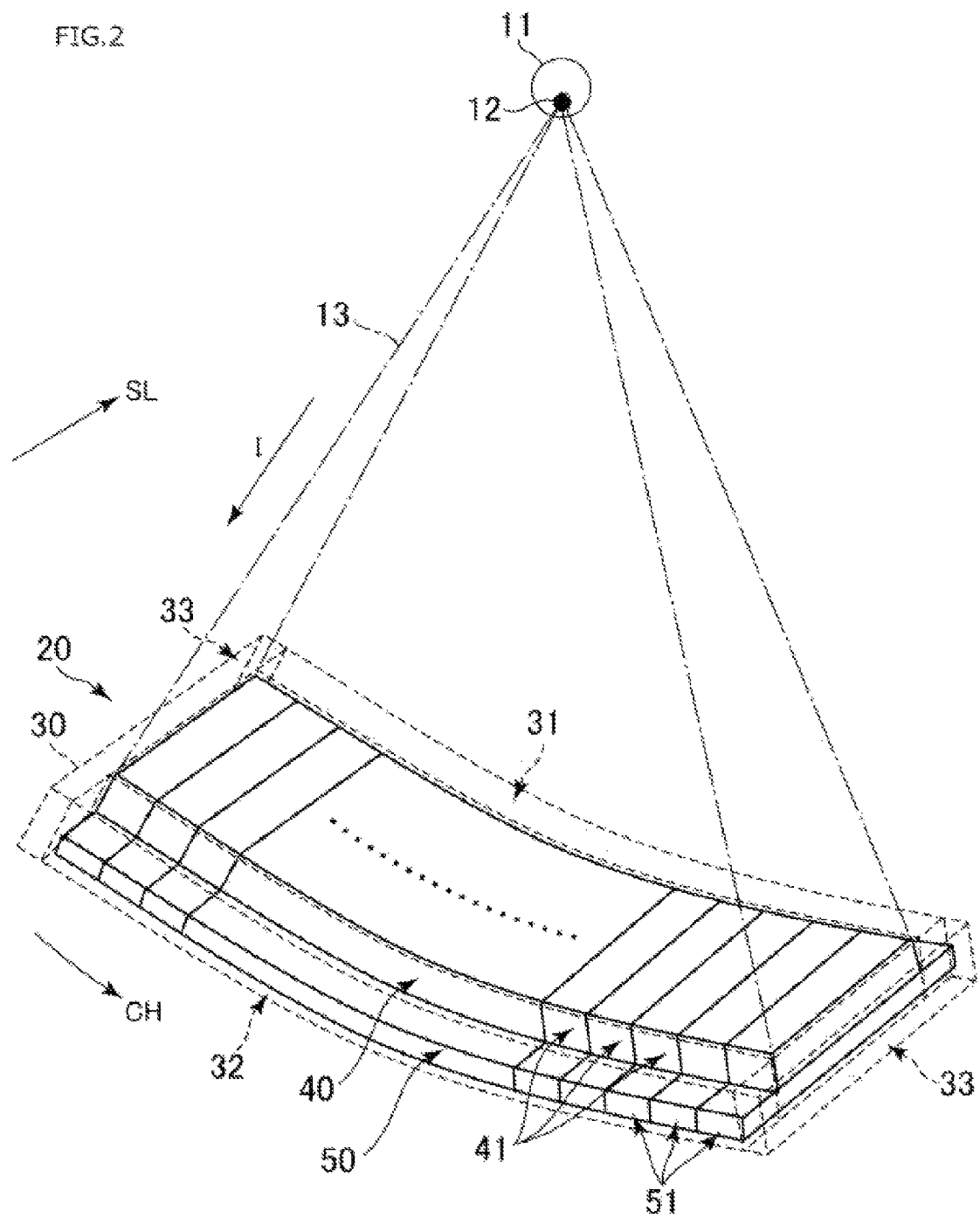
FIG. 2 is a diagram schematically illustrating a configuration of a scan gantry.

FIG. 2 is a diagram schematically showing the configuration of the X-ray detecting apparatus. As shown in FIG. 2, the X-ray detecting apparatus 20 has a frame (support part) 30, a collimator device 40 and an X-ray detector 50. The frame 30 is provided to fix each of the collimator device 40 and the X-ray detector 50 to a reference position and support them. The collimator device 40 is provided to collimate the X-rays 13 radiated from the X-ray focal point 12 of the X-ray tube 11 and mainly eliminate scattered radiation. The X-ray detector 50 is provided to detect the X-rays 13 irradiated from the X-ray focal point 12 of the X-ray tube 11 and transmitted through the subject 9. The X-ray detector 50 is placed on the X-ray outgoing side of the collimator device 40.

The frame 30 has a frame-like shape that assumes a rectangle as seen in the I direction. The frame 30 has a top side rail 31 and a bottom side rail 32 (a pair of rails), and a pair of connecting parts 33. The top side rail 31 and the bottom side rail 32 both have an arc shape that extends in the CH direction. The top side rail 31 and the bottom side rail 32 are disposed with being spaced away from each other as viewed in the SL direction and are coupled and fixed to each other through the connecting parts 33 at both ends as viewed in the CH direction. The top side rail 31 and the bottom side rail 32 are formed so as to be symmetrical about the plane in the SL direction. The top side rail 31 and the bottom side rail 32 are comprised of a high rigidity material such as Al (aluminum), SUS (stainless), C (carbon) or the like.

The collimator device 40 is made up of a plurality of collimator modules 41 arranged along the CH direction.

The X-ray detector 50 is made up of a plurality of detector modules 51 arranged along the CH direction.

Figure 3B:
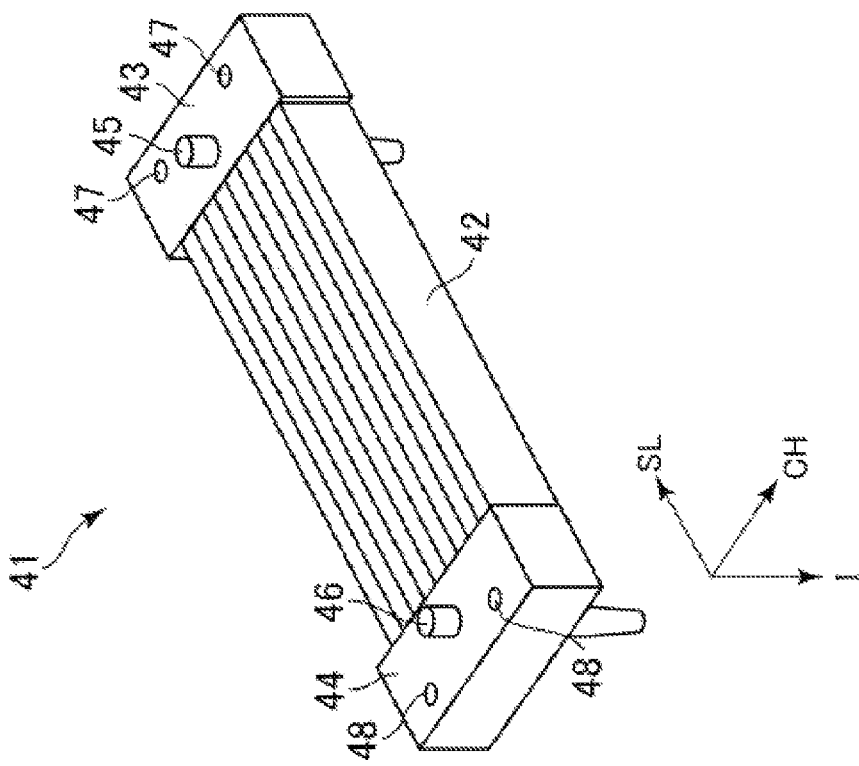
FIGS. 3A and 3B are diagrams depicting a configuration of a collimator module.
Figure 3A:
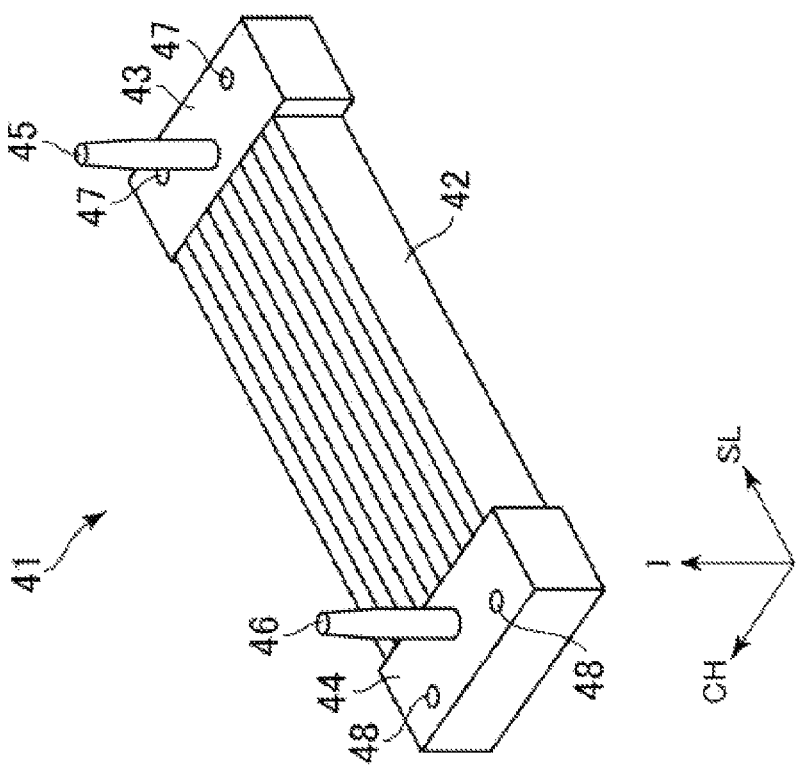

FIGS. 3A and 3B are diagrams showing the configuration of the collimator module 41. FIG. 3A is a perspective diagram of the collimator module 41 as viewed from the X-ray outgoing side, and FIG. 3B is a perspective diagram of the collimator module 41 as viewed from the X-ray incoming side.

As shown in FIGS. 3A and 3B, the collimator module 41 includes a plurality of collimator plates 42 arranged in the CH direction, and a top side block 43 and a bottom side block 44 which support these collimator plates 42 with the collimator plates 42 interposed therebetween as viewed in the SL direction. A top side alignment pin 45 is provided in the neighborhood of the center of the top side block 43 as viewed in the CH direction. Likewise, a bottom side alignment pin 46 is provided in the neighborhood of the center of the bottom side block 44 as viewed in the CH direction. Each of the top side and bottom side alignment pins 45 and 46 has an approximately cylindrical form that extends along the I direction. The top side and bottom side alignment pins 45 and 46 are press-fitted in and fixed to through holes defined in the centers of the top side and bottom side blocks 43 and 44 as viewed in the CH direction. Each of the collimator plates 42 is comprised of a heavy metal high in X-ray absorptivity, such as tungsten (W), molybdenum (Mo) or the like. The top side and bottom side blocks 43 and 44, and the top side and bottom side alignment pints 45 and 46 are comprised of, for example, stainless, aluminum or the like. Incidentally, the collimator modules 41 are configured so as to separate detecting elements corresponding to 32 cells in the CH direction.

FIGS. 4A and 4B are diagrams showing the configuration of the detector module 51. FIG. 4A is a perspective diagram of the detector module 51 as viewed from the X-ray outgoing side, and FIG. 4B is a perspective diagram of the detector module 51 as viewed from the X-ray incoming side.

As shown in FIGS. 4A and 4B, the detector module 51 is made up of a plurality of detecting elements 52 two-dimensionally arranged in the CH and SL directions, and a support body 53 which supports these detecting elements 52. A signal processing unit for processing signals outputted from the detecting elements 52 may be fixed to the support body 53. Top side mounting holes 56 and bottom side mounting holes 57 for mounting the collimator module 51 to the top side and bottom side rails 31 and 32 are formed at both ends in the SL direction, of the support body 53. Top side and bottom side alignment holes 54 and 55 into which the top side and bottom side alignment pins 45 and 46 are fitted, are formed in positions close to both ends in the SL direction, of the support body 53 and being in close proximity to the center thereof in the CH direction. The pitch of arrangement of the detecting elements 52 is 1 mm, for example. The detecting element 52 includes, for example, a scintillator element which emits light in response to the X-rays 13, and a photo diode which performs photoelectric conversion. The support body 53 includes, for example, stainless, aluminum or the like. The detector module 51 is configured by arranging the detecting elements 52 corresponding to 32 cells in the CH direction and 64 cells in the SL direction, for example.

FIG. 5 is a diagram showing the manner in which each of the collimator modules is positioned using the alignment pins. This diagram is shown as a perspective diagram taken when the top side and bottom side rails 31 and 32 are seen from the X-ray outgoing side.

As shown in FIG. 5, a top side first plane 311, a top side first curved plane 312, a top side second plane 313, and a top side second curved plane 314 are stepwise formed in the top side rail 31. Likewise, a bottom side first plane 321 (not shown), a bottom side first curved plane 322 (not shown), a bottom side second plane 323 (not shown), and a bottom side second curved plane 324 are stepwise formed even in the bottom side rail 32. The top side and bottom side first planes 311 and 321 and the top side and bottom side second planes 313 and 323 are approximately parallel to the I direction corresponding to the X-ray radiation direction. The top side and bottom side first planes 311 and 321 and the top side and bottom side second planes 313 and 323 both formed in the top side and bottom side rails 31 and 32 are respectively formed opposite to each other in the SL direction. The top side and bottom side first curved planes 312 and 322 are respectively placement surfaces on which the collimator modules 41 are placed.

A plurality of top side and bottom side concave grooves 34 and 35 (not shown in FIG. 5) in which the top side and bottom side alignment pins 45 and 46 provided in the collimator modules 41 are fitted, are formed in the top side and bottom side first planes 311 and 321 and the top side and bottom side first curved planes 312 and 322 at intervals in the CH direction. A plurality of top side and bottom side first threaded holes 361 and 371 (not shown in FIG. 5) for fastening the collimator modules 41 with screws are respectively formed in the top side and bottom side first curved planes 312 and 322. A plurality of top side and bottom side second threaded holes 362 and 372 for fastening the detector modules 51 with screws are respectively formed in the top side and bottom side second curved planes 314 and 324. Incidentally, these concave grooves and threaded holes are formed by being highly accurately dug in members forming the top side rail 31 and the bottom side rail 32 with a drill or the like. Other parts formed with these concave grooves and threaded holes may be attached to the top side rail 31 and the bottom side rail 32, but they are directly dug in the rails in the exemplary embodiment because high rigidity is obtained.

Each of the collimator modules 41 is arranged in such a manner that the ends on the X-ray incoming side, of the top side and bottom side alignment pins 45 and 46 thereof are respectively fitted into the top side and bottom side concave grooves 34 and 35. Thus, the collimator module 41 is positioned relative to the top side rail 31 and the bottom side rail 32. The collimator module 41 is threadedly mounted in the top side and bottom side first threaded holes 361 and 371 in this state.

FIG. 6 is a diagram showing the manner in which the detector module is positioned using the alignment pins. As with FIG. 5, this diagram is shown as a perspective diagram taken when the top side and bottom side rails 31 and 32 are seen from the X-ray outgoing side.

Each of the detector modules 51 is arranged in such a manner that the ends on the X-ray outgoing side, of the top side and bottom side alignment pins 45 and 46 are respectively fitted into the top side and bottom side alignment holes 54 and 55 of the detector module 51. Thus, the detector module 51 is positioned relative to the top side rail 31 and the bottom side rail 32. The detector module 51 is threadedly mounted in the top side and bottom side second threaded holes 362 and 372 in this state.

Figure 7:
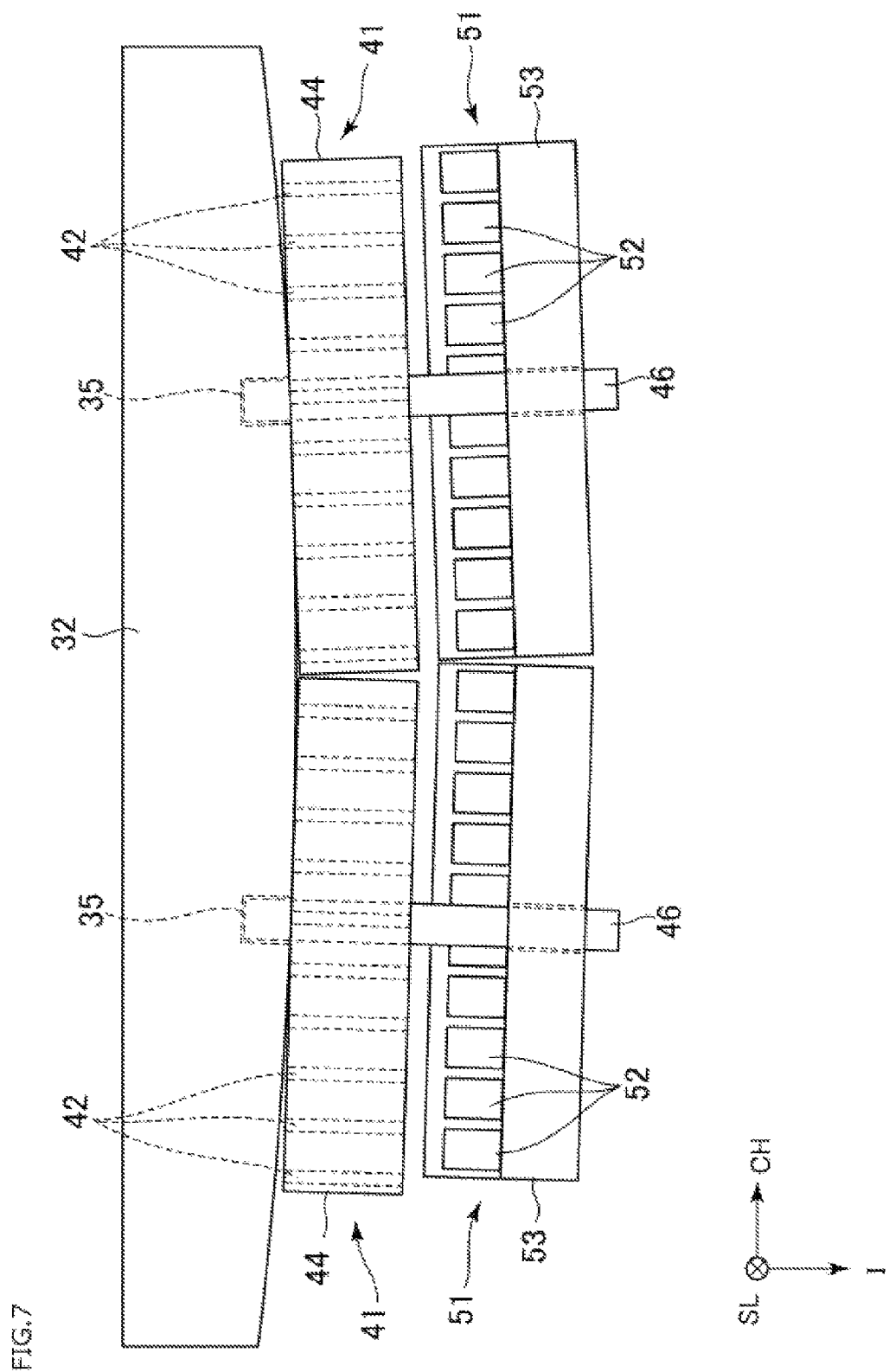
FIG. 7 is a diagram showing the manner in which the collimator modules and the detector modules are respectively positioned relative to rails.

FIG. 7 is a diagram showing the manner in which the collimator modules and the detector modules are respectively positioned relative to the rails. This diagram is shown as a diagram taken when the top side rail 31 and the bottom side rail 32 are seen in the SL direction.

When the collimator modules 41 and the detector modules 51 have respectively been positioned, the collimator plates 42 have been designed in such a manner as to separate the detecting elements 52 in the CH direction with high accuracy. When, however, the collimator module 41 or the collimator plates 42 are placed even in both positions corresponding to both ends of each detecting element 53 in the detector module 51 as viewed in the CH direction, the collimator plates 42 overlap each other at a joint between the detector modules 51. Therefore, actually, the collimator module 41 is designed in such a manner that the collimator plate 42 is placed only in one of the positions corresponding to both ends of the detecting element 52 in the detector module 51 as viewed in the CH direction. On the other hand, the top side and bottom side alignment holes 54 and 55 of the detector module 51 are arranged in the center in the CH direction, of the detector module 51 because of their ease of design and so on. Therefore, the top side and bottom side alignment pins 45 and 46 of each collimator module 41 are placed in positions which are located in the neighborhood of the CH-direction center of the collimator module 41, i.e., the top side and bottom side blocks 43 and 44 are slightly shifted in the CH direction from the center thereof.

According to the exemplary embodiment as described above, since the collimator module 41 and the detector module 51 that correspond to each other are positioned on the basis of the top side and bottom side alignment pins 45 and 46 identical to each other, the accumulation of tolerances at their positioning can be prevented, and the detecting elements 52 and the collimator plates 42 can highly accurately be aligned with each other.

Incidentally, the disclosure is not limited to the exemplary embodiment, and various embodiments can be adopted within the scope of the disclosure without departing from the gist invention.

For example, the top side and bottom side concave grooves 34 and 35 respectively formed in the top side and bottom side first planes 311 and 321 may be provided as columnar concave holes instead.

Also, for example, the top side and bottom side alignment holes 54 and 55 formed in the detector module 51, which are fitted to the ends on the X-ray outgoing side, of the top side and bottom side alignment pins 45 and 46, may be provided as concave holes having ends instead of the through holes.

Further, for example, the sectional shape of each of the top side and bottom side alignment pins 45 and 46 may be not only a perfect circular form, but also an elliptic shape, a polygon or the like.

Furthermore, for example, the collimator module 41 may be a two-dimensional collimator module in which the collimator plates 42 are arranged in lattice form in the CH and SL directions.

Still further, for example, the disclosure is not limited to an apparatus using the X-rays, but can be applied even to an apparatus using other radiation, e.g., γ (gamma) rays as in an SPECT apparatus.

What is claimed is:
1. A radiation detecting apparatus comprising:
a pair of rails extending in a channel direction;
a plurality of collimator modules provided in the pair of rails and arranged in the channel direction, each collimator module having a plurality of collimator plates arranged in the channel direction; and
a plurality of detector modules provided on a radiation outgoing side of the collimator modules and arranged in the channel direction, each detector module having a plurality of detecting elements arranged in the channel direction,
wherein each of the collimator modules has a pair of alignment pins extending along an irradiation direction of radiation,
wherein the rails include a surface of placement for each collimator module, the surface of placement formed with one of concave holes and grooves in which first ends of the alignment pins are fitted, and
wherein each of the detector modules has one of concave holes and through holes in which second ends of the alignment pins are fitted.

2. The radiation detecting apparatus according to claim 1, wherein the one of concave holes and grooves in the rails are formed by being dug out of members which form the rails.

3. The radiation detecting apparatus according to claim 1, wherein each of the collimator modules is fastened to the rails with screws in a state in which the first ends of the alignment pins have been fitted in the one of concave holes and grooves of the rails.

4. The radiation detecting apparatus according to claim 1, wherein each of the detector modules is fastened to the rails with screws in a state in which the second ends of the alignment pins have been fitted in the one of concave holes and through holes of each of the detector modules.

5. The radiation detecting apparatus according to claim 1, wherein the alignment pins are located in positions proximate to a center of the corresponding collimator module in the channel direction and shifted in the channel direction from the center.

6. The radiation detecting apparatus according to claim 1, wherein each of the collimator modules has a pair of blocks which support the collimator plates such that the collimator plates extend in a slice direction between the pair of blocks, and
wherein the alignment pins are provided in the pair of blocks.

7. The radiation detecting apparatus according to claim 6, wherein the alignment pins are press-fitted into and fixed to through holes formed in the pair of blocks.

8. The radiation detecting apparatus according to claim 1, wherein the rails have planes that oppose each other in the slice direction, and
wherein the concave grooves are formed by being dug in the placement surfaces and the planes.

9. The radiation detecting apparatus according to claim 1, wherein each of the detector modules has a support body which supports the detecting elements and a signal processing unit configured to process signals outputted from the detecting elements, and
wherein the one of concave holes and through holes of each of the detector modules are formed in the support body.

10. A radiation imaging apparatus including a radiation detecting apparatus comprising:
a pair of rails extending in a channel direction;
a plurality of collimator modules provided in the pair of rails and arranged in the channel direction, each collimator module having a plurality of collimator plates arranged in the channel direction; and
a plurality of detector modules provided on a radiation outgoing side of the collimator modules and arranged in the channel direction, each detector module having a plurality of detecting elements arranged in the channel direction, wherein each of the collimator modules has a pair of alignment pins extending along an irradiation direction of radiation, wherein the rails include a surface of placement for each collimator module, the surface of placement formed with one of concave holes and grooves in which first ends of the alignment pins are fitted, and wherein each of the detector modules has one of concave holes and through holes in which second ends of the alignment pins are fitted.

11. The radiation imaging apparatus according to claim 10, wherein the one of concave holes and grooves in the rails are formed by being dug in members which form the rails.

12. The radiation imaging apparatus according to claim 10, wherein each of the collimator modules is fastened to the rails with screws in a state in which the first ends of the alignment pins have been fitted in the one of concave holes and grooves of the rails.

13. The radiation imaging apparatus according to claim 10, wherein each of the detector modules is fastened to the rails with screws in a state in which the second ends of the alignment pins have been fitted in the one of concave holes and through holes of each of the detector modules.

14. The radiation imaging apparatus according to claim 10, wherein the alignment pins are located in positions proximate to a center of the corresponding collimator module in the channel direction and shifted in the channel direction from the center.

15. The radiation imaging apparatus according to claim 10, wherein each of the collimator modules has a pair of blocks which support the collimator plates such that the collimator plates extend in a slice direction between the pair of blocks, and wherein the alignment pins are provided in the pair of blocks.

16. The radiation imaging apparatus according to claim 15, wherein the alignment pins are press-fitted into and fixed to through holes formed in the pair of blocks.

17. The radiation imaging apparatus according to claim 10, wherein the rails have planes that oppose each other in the slice direction, and wherein the concave grooves are formed by being dug in the placement surfaces and the planes.

18. The radiation imaging apparatus according to claim 10, wherein each of the detector modules has a support body which supports the detecting elements and a signal processing unit configured to process signals outputted from the detecting elements, and wherein the one of concave holes and through holes of each of the detector modules are formed in the support body.

19. The radiation imaging apparatus according to claim 10, wherein the radiation imaging apparatus is configured to perform radiation tomographic imaging.

20. A method of assembling a radiation detecting apparatus, said method comprising:

providing a pair of rails extending in a channel direction, the rails including a surface of placement formed with one of concave holes and grooves;

providing a plurality of collimator modules, each collimator module including a pair of alignment pins and a plurality of collimator plates;

coupling the plurality of collimator modules to the pair of rails by inserting first ends of the alignment pins into the one of concave holes and grooves formed in the surface of placement, the plurality of collimator modules coupled to the pair of rails such that the plurality of collimator modules and the plurality of collimator plates are arranged in the channel direction, and the alignment pins extend in an irradiation direction of radiation; and coupling the plurality of collimator modules to a plurality of detector modules by inserting second ends of the alignment pins into one of concave holes and through holes formed in the plurality of detector modules, wherein the detector modules include a plurality of detecting elements arranged in the channel direction.

* * * * *